United States Patent [19]

Thompson

[11] 4,014,973
[45] Mar. 29, 1977

[54] METHOD OF COMPACTING SILK SUTURES BY STRETCHING

[75] Inventor: Darrell R. Thompson, Somerville, N.J.

[73] Assignee: Ethicon, Inc., Somerville, N.J.

[22] Filed: July 31, 1973

[21] Appl. No.: 384,318

[52] U.S. Cl. .................. 264/290 R; 128/335.5
[51] Int. Cl.² ............. B29C 17/02; A61L 17/00
[58] Field of Search ....... 264/290 R, 290 N, 290 T, 264/DIG. 73, 340, 233; 128/335.5; 28/76 R; 87/1

[56] References Cited

UNITED STATES PATENTS

| | | | |
|---|---|---|---|
| 2,918,346 | 12/1959 | Paulsen | 28/76 R |
| 2,948,581 | 8/1960 | Cummings, Jr. | 264/DIG. 73 |
| 3,098,696 | 7/1963 | Ball et al. | 264/340 |
| 3,259,681 | 7/1966 | Bull et al. | 264/210 F |
| 3,424,164 | 1/1969 | Block et al. | 128/335.5 |
| 3,567,817 | 3/1971 | Spiller | 264/290 T |
| 3,657,409 | 4/1972 | Ram et al. | 264/210 F |

FOREIGN PATENTS OR APPLICATIONS

| | | | |
|---|---|---|---|
| 241,599 | 4/1960 | Australia | 128/335.5 |
| 349,232 | 5/1931 | United Kingdom | 28/76 R |
| 762,938 | 12/1956 | United Kingdom | 128/335.5 |

*Primary Examiner*—Robert F. White
*Assistant Examiner*—James B. Lowe
*Attorney, Agent, or Firm*—Wayne R. Eberhardt

[57] ABSTRACT

Braided silk surgical sutures having increased tensile strength and knot strength are prepared by (1) pre-soaking conventionally-prepared unstretched braided silk sutures in a non-corrosive liquid (preferably water) for at least about 30 minutes to wet the silk fibers, (2) stretching the presoaked sutures while the same are immersed in a non-corrosive liquid (preferably water), and then (3) drying the stretched silk sutures while maintaining the stretched length and not allowing shrinkage to occur during drying. The wet-stretching method of the invention makes possible the stretching of braided silk sutures to a greater extent than that obtainable by conventional hot-stretching techniques, up to about 2½ times greater, without damage to the sutures. The wet-stretched sutures of the invention have greater tensile strength and knot strength than the prior art hot-stretched sutures of comparable diameter.

3 Claims, 3 Drawing Figures

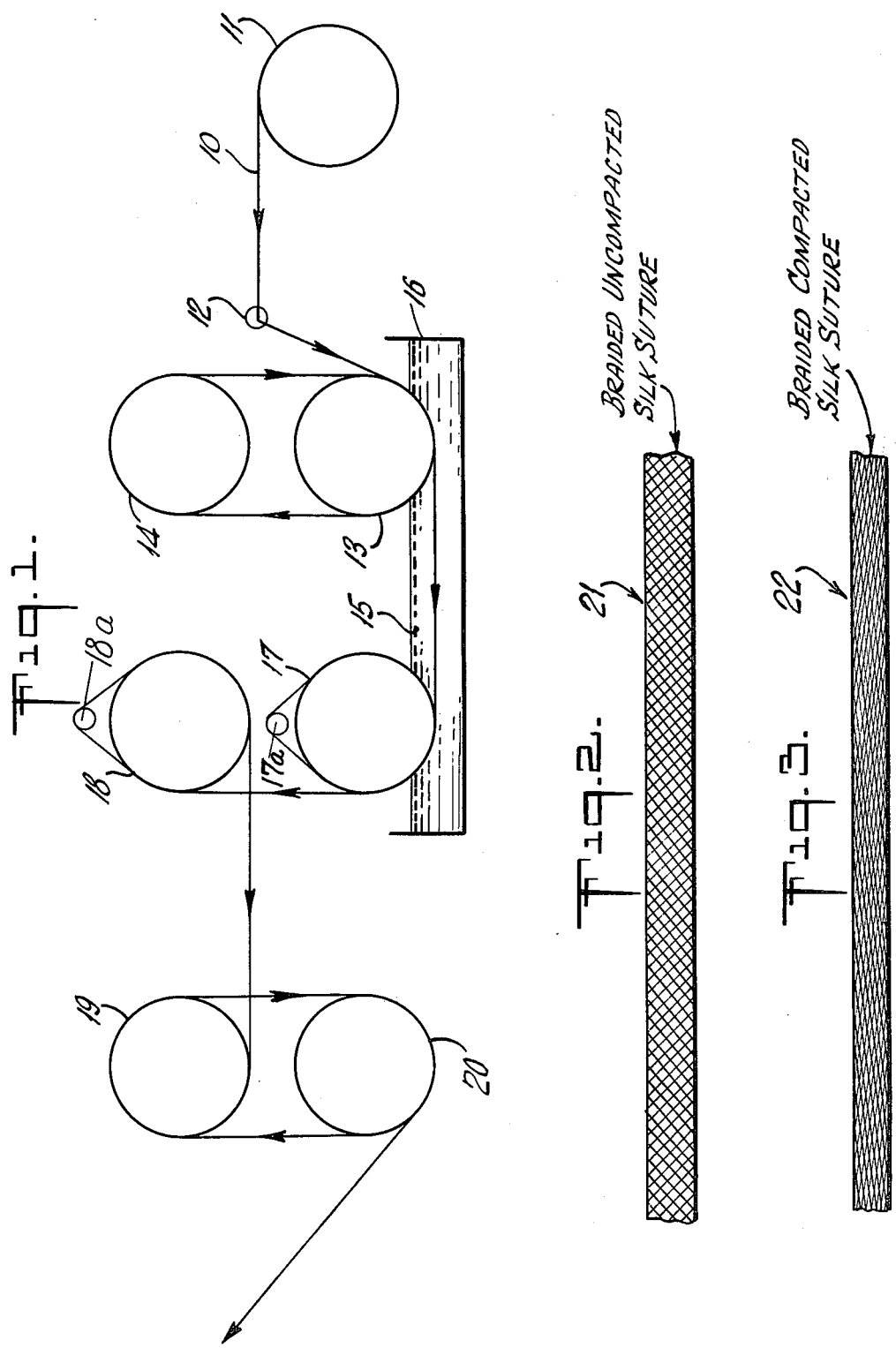

METHOD OF COMPACTING SILK SUTURES BY STRETCHING

BACKGROUND OF THE INVENTION

This invention relates to sutures and more particularly to compacted braided silk sutures of increased tensile strength and knot strength, and to methods of making the same.

In the suture art, the term "braided suture" means a substantially symmetrical strand formed by crossing a number (at least three) of individual strands, called "carriers", composed of one or more threads diagonally in such a manner that each strand passes alternatively over and under one or more of the others. The braided suture may, if desired, include a core section composed of one or more threads around which the braid is externally fabricated.

The term "uncompacted braided suture" means a braided suture which has not been subjected to any compacting force following its preparation and which is characterized by a relatively loosely braided structure.

The term "compacted braided suture" means a braided suture which has been subjected to a stretching force or other compacting force whereby the diameter of the suture has been decreased.

Uncompacted braided silk sutures of the prior art have customarily been stretched under the influence of heat to decrease the diameter of the suture by making it more compact and consequently to increase its strength per square inch. These stretched braided silk sutures offer many advantages over unstretched sutures. Stretching of the suture makes it possible to prepare the strongest suture for a given suture diameter. By compacting the braided suture and thus reducing the volume of the voids therein, it becomes possible to increase the number of threads within a given diameter. In effect, the cross-section of the compacted braided silk suture approaches that of a monofilament.

Compacted braided silk sutures have advantages over monofilament sutures, notably in their flexibility and dependability. Another advantage of compacted braided silk sutures is that the compact nature of the braid reduces capillarity, which in turn inhibits the spread of infection along the suture. The tightness of the braid also reduces an undesirable "brooming" effect, i.e., the flaring of individual threads of the braided suture when the same is cut. Further, because of the smoother surface of the compacted braided silk suture resulting from the stretching operation, less tissue trauma is likely to occur from the use thereof.

The effectiveness of any method of stretching braided sutures is limited by the percentage stretch which can be achieved without substantially damaging the threads of the suture. The greater the percentage stretch without damaging the threads, the greater the decrease in diameter of the suture and the greater the increase in tensile strength and knot strength per square inch—which criteria characterize a suture. In general, the hot-stretching technique of the prior art as applied to silk sutures is limited to a percentage stretch of about 5–10%, since silk fibers are not thermoplastic. Stretching substantially beyond 10% by the hot-stretching technique of the prior art results in substantial fiber breakage and, consequently, in a weaker, fuzzy suture. Thus, hot-stretching of silk without damage to the fibers is severely limited in the percentage stretch which can be obtained thereby.

SUMMARY OF THE INVENTION

According to the present invention, braided silk sutures which have been presoaked in a non-corrosive liquid to wet the silk fibers can be stretched while immersed in a non-corrosive liquid up to about 35% without fiber damage and can be set in this stretched condition by drying the stretched suture while maintaining the same under tension, thereby increasing the tensile strength and knot strength of the suture substantially above that obtainable by prior art techniques. It is to be noted, in particular, that the wet-stretched and tension-dried braided silk sutures which are the product of the invention exhibit a known strength on the order of 10–15% greater than that of conventionally hot-stretched sutures of comparable diameter.

In carrying out the method of my invention a conventionally produced, unstretched, braided silk suture is presoaked in a non-corrosive liquid, preferably water, for at least about one-half hour, preferably in the range of from about three to about eight hours, to wet the silk fibers. The presoaked suture is then stretched in the range of from about 5 to about 35% of its original length, while the same is immersed in a non-corrosive liquid, which liquid may be the same as was used for the presoaking operation or may be different, but preferably is water. After the suture is stretched, it is removed from the immersion tank and is dried under tension, adequate to prevent shrinkage during the drying step. It is then processed according to conventional procedures (e.g., waxed, sterilized, etc., cut into suitable lengths, and packaged).

It is believed, without intending to be bound thereby, that the theoretical basis by which the wet-stretching and tension-drying process of my invention produces the improved properties which characterize the novel braided silk suture of my invention is that the silk threads are plasticized during the presoaking and the immersion and stretching steps. During the presoaking step, the silk fibers are penetrated by the liquid, thus making them more flexible and able to be stretched without damage to a greater extent than heretofore. The stretched silk fibers removed from the immersion tank are set in their stretched form outside of the immersion tank, by drying the same under tension, maintaining the stretched length constant thus preventing shrinkage during the drying step.

While the preferred presoaking and immersion liquids are water, any other non-corrosive liquids may be used in these steps, e.g., alcohols, such as ethanol, methanol and propanol, ketones such as acetone and methyl ethyl ketone, and like low viscosity, non-corrosive liquids that will wet the silk threads.

It is not amiss to point out that the prior art discloses the use of water as a surface lubricant in the stretching of synthetic yarns and filaments, but insofar as I am aware, the prior art does not teach the wet-stretching of braided natural fibers such as silk, and the subsequent drying thereof under tension, as in my invention.

It is contemplated that the method of the present invention may be practiced in various ways. Thus, any stretching technique which effects the desired elongation of the silk suture may be used. Stretching of the braided silk suture between conventional Godet rolls rotating at different speeds is the preferred method. Any means of drying the stretched suture under tension may be used. While drying on a heated, revolving conventional Godet roll is illustrated as the preferred drying method herein, other methods, such as passage through a tube filled with hot air or over a hot plate, may be used so long as tension on the stretched suture is maintained during the drying process.

The presoaking and immersion stretching operations may take place in the non-corrosive liquid at ambient temperatures. It will be understood, of course, that the temperature used must be above the freezing point of the liquid and substantially below its boiling point. When water is the liquid used, the preferred temperature for both presoaking and immersion stretching is in the range of from about 70° to about 80° F., but the use of the elevated temperatures, say up to about 180° F., is acceptable. Such elevated temperatures allow shorter presoaking time and more rapid travel of the suture through the stretching tank than would be necessary if the non-corrosive liquid were not heated.

The invention will be more fully described in the accompanying drawings in which:

FIG. 1 diagrammatically depicts apparatus which may be used to carry out the method of the invention for producing the product of the invention;

FIG. 2 is an enlarged elevational side view of an uncompacted braided silk suture; and FIG. 3 is an enlarged elevational side view of a compacted silk suture which is the product of the invention.

Referring to FIG. 1, the presoaked uncompacted braided silk suture 10 (either still wet from the presoaking step or dry from a subsequent drying step), is fed from feed spool 11 through guide 12 and is caused to travel several times about unheated rotatable Godet rolls 13 and 14, which are fixedly positioned one above the other and which serve as they rotate at the same speed to draw the suture from the spool.

Lower Godet roll 13 is positioned so that at least a portion thereof is immersed as it rotates in non-corrosive liquid 15 in trough 16, and thus provides an anchoring means for insuring that the suture is stretched while immersed in said liquid, as hereinafter described. After the repeated travels of the suture about Godet rolls 13 and 14, the free end of the suture is drawn off from lower Godet roll 13 while the suture is immersed in the liquid. While still within the liquid, the suture is threaded for travel several times about lower unheated rotatable Godet roll 17 and idler roll 17a which are fixedly positioned with respect to upper rotatable heated Godet roll 18 and idler roll 18a, rolls 17 and 17a rotating at a faster speed than Godet rolls 13 and 14. In its travel, the suture is repeatedly immersed in the liquid by virtue of the positioning of lower Godet roll 17 so that a portion thereof is immersed in the liquid as it rotates.

The stretching of the suture occurs between lower Godet roll 13 and lower Godet roll 17 by virtue of the differences in the peripheral speeds thereof, while the same is immersed in liquid 15, as hereinafter described. To go on with the description of the operation, the suture is caused to travel several times about lower Godet roll 17 and idler roll 17a, and is then conducted to drying Godet roll 18, which rotates at no less than the same speed as Godet roll 17, to maintain tension on the wet, stretched suture. The stretched suture is caused to travel several times about drying Godet roll 18 and idler roll 18a, until the same is dried. The dry, stretched suture is then conducted to unheated, rotatable Godet rolls 19 and 20, fixedly secured one above the other, and is caused to travel several times about these rolls to maintain tension on the suture as it travels about drying Godet roll 18. From Godet rolls 19 and 20, the suture travels to a wind-up bobbin (not shown).

The Godet rolls hereinabove referred to are of known construction and are conventionally used in the suture and textile arts to carry threads or filaments without entanglement. As is known, they are horizontally mounted with an inclination oblique to the direction of travel of the thread or filament, to accomplish this purpose. The mounting of the Godet rolls in the apparatus illustrated diagrammatically in FIG. 1 is conventional to insure that there will be no entanglement of the suture as it is being processed thereon in accordance with the method of my invention. Because of this and because the apparatus per se forms no part of my invention and is not claimed herein, further details of these rolls and their operation are omitted to avoid undue enlargement of the description of my invention.

The peripheral speed of rotation of Godet rolls 13 and 14 is the same and is lower than that of Godet roll 17 according to the stretch desired. Drying Godet roll 18 may be rotated at the same peripheral speed as or slightly faster than Godet roll 17 to maintain tension on the wet, stretched suture. Godet rolls 19 and 20 are rotated at the same peripheral speed, which speed is faster (preferably about 1% faster) than that of drying Godet roll 18 to maintain the suture under tension while the same is drying. The rate of speed at which the suture travels through liquid 15 during the immersion stretching step is not critical. Although good results are obtained at rates of speed between about 65 and about 75 feet/minute when the liquid is water, it is contemplated that rates of speed of the suture through the liquid of up to about 500 feet/minute may be used.

Godet rolls 13 and 14 are preferably rotated at a peripheral speed in the range of from about 60 feet/minute to about 75 feet/minute, Godet roll 17 is preferably rotated at a peripheral speed in the range of from about 72 feet/minute to about 78 feet/minute, drying Godet roll 18 is preferably rotated at a peripheral speed in the range of from about 72 feet/minute to about 78 feet/minute, and Godet rolls 19 and 20 are preferably rotated at a peripheral speed in the range of from about 72 feet/minute to about 79 feet/minute, according to the percentage stretch desired in the stretched suture. These ranges of peripheral speed cause the suture to travel through the liquid at the preferred rate of speed, when the liquid is water, of from about 65 feet/minute to about 75 feet/minute. Although the ranges of peripheral speeds for the Godet rolls disclosed above are preferable, it is contemplated that peripheral speeds of the Godet rolls up to about 500 feet/minute may be used, to cause the suture to travel through the liquid at a rate of speed up to about 500 feet/minute.

In the preferred embodiment of the method of my invention, the suture is wrapped six times about Godet rolls 13 and 14; 5 times about Godet roll 17 and idler roll 17a; nine or ten times about drying Godet roll 18 and idler roll 18a; and 8 times about Godet rolls 19 and 20. The number of wraps is not critical except for drying Godet roll 18, as is discussed below. Because the purpose of the wrapping of the suture about the Godet rolls other than Godet roll 18 is only to prevent slippage thereof about the Godet rolls during the operation of the apparatus, any number of wraps which accomplishes this purpose may be used.

Drying Godet roll 18 may be heated in the range of from about 70° to about 300° F., preferably to about 250° F., to effect drying of the suture. In the preferred embodiment of the method of my invention, drying Godet roll 18 has a diameter of approximately 6 inches; therefore, nine wraps of stretched suture yields approximately 14 ft. of suture contact therewith. If drying Godet roll 18 is rotated within its preferred range of peripheral speeds, say at a peripheral speed of 75 feet/minute, then the residence time of any one portion of the suture thereon is about 20 seconds. At the preferred drying temperature of about 250° F., this residence time of the stretched suture on drying Godet roll 18 is sufficient to dry the suture completely. Because the residence time of the stretched suture on drying Godet roll 18 required for complete drying thereof is dependent upon the amount of suture contact with drying Godet roll 18 as well as on the peripheral speed of rotation of said roll, there is a critical number of wraps about drying Godet roll 18 for a particular roll size and peripheral speed of rotation, below which number of wraps the suture will not completely dry. Because the suture must be dried while maintained under tension, it is critical to the method of my invention in the preferred embodiment that the suture be wrapped a sufficient number of times about drying Godet roll 18 to effect complete drying at the particular peripheral speed of drying Godet roll 18 being used.

Any alternative method of drying, such as passing the stretched suture through a tunnel containing hot air, which accomplishes the purpose of drying the stretched suture while maintaining the same under tension can be used in place of drying Godet roll 18. If such an alternative method were used, drying Godet roll 18 would be unheated and the alternative drying method would be placed between drying Godet roll 18 and Godet roll 19 and the wet, stretched suture would pass through the same. In such a case, the number of wraps of stretched suture about drying Godet roll 18 and idler roll 18a would not be critical.

Referring to FIGS. 2 and 3, there is illustrated therein the difference between a conventionally-prepared uncompacted braided silk suture 21 and a compacted braided silk suture 22, wet-stretched and tension-dried according to the method of my invention.

The product of my invention exhibits greater knot strength and tensile strength than have heretofore been obtained in prior art sutures of comparable diameter. Because it is the knot which is the weakest part of a suture when in use, increases in knot strength are of great significance. The product of my invention has a knot strength in a range of from about 10 to about 20% greater than has heretofore been obtainable in a braided silk suture.

The following examples illustrate the manufacture of several embodiments of the present invention.

EXAMPLE I

A conventional black-dyed uncompacted, braided silk suture, composed of a core (2 cords of 2 threads each) and eight carriers (each carrier having 2 cords and each cord having 4 threads), which structure will be represented hereinafter as "8 carrier — 4 × 2 (13/15); core — 2 × 2 (13/15)," was divided into two portions. One portion was conventionally hot-stretched over a hot plate at a temperature of about 375° F. at a speed of travel of said suture over said hot plate of from about 200 feet/minute to about 225 feet/minute, causing a suture stretch of approximately 8%.

The other portion was presoaked in room-temperature water for five hours, and was then wet-stretched on the apparatus depicted in FIG. 1 using water at 82° F. as the immersion solvent. The suture was wrapped 6 times about Godet rolls 13 and 14, five times about Godet roll 17 and idler roll 17a; nine times about drying Godet roll 18 and idler roll 18a; and eight times about Godet rolls 19 and 20. Godet rolls 13 and 14 were rotated at a peripheral speed of 61 feet/minute, Godet roll 17 at 72.5 feet/minute, drying Godet roll 18 at 73 feet/minute, and Godet rolls 19 and 20 at 76 feet/minute. Drying Godet roll 18 was heated to about 250° F. A suture stretch of approximately 19% resulted from this treatment.

The two stretched portions were waxed and sterilized by $Co_{60}$ radiation and were then measured and tested for tensile strength and knot strength. The results are shown in Table I. The wet-stretched suture exhibited a 13.5% greater knot strength (psi) than the hot-stretched suture.

EXAMPLE II

The procedure of Example I was repeated using a 16 carrier — 2 × 2 (13/15); core — 10 × 3 (13/15) black dyed, braided silk suture. One portion was hot-stretched 8% as before; the other was wet-stretched 15% substantially as before. The presoak liquid, time and temperature, the immersion liquid and temperature, the temperature of drying Godet roll 18, and the wrapping arrangement were kept the same. The peripheral speed of Godet rolls 13 and 14 was 63 feet/minute, that of Godet roll 17 was 72 feet/minute, that of drying Godet roll 18 was 72 feet/minute, and that of Godet rolls 19 and 20 was 72.5 feet/minute. Both portions were then waxed and $Co_{60}$ sterilized before being measured and tested.

The results of the measurement and testing are shown in Table I. The wet-stretched suture exhibited a 13.0% greater knot strength (psi) than the hot-stretched suture.

EXAMPLE III

The procedure of Example I was repeated for three pairs of sutures so constructed that the final diameters of the hot-stretched and wet-stretched member of each pair were comparable. The hot-stretched suture was stretched as in Example I. The wet-stretched suture was stretched generally as in Example I with the operating conditions being given in Table II. After stretching, the three pairs were close to the maximum diameters for sizes 2-0, 4-0, and 2 sutures, respectively.

TABLE I
Black braided silk, stretched, waxed, and C060 sterilized

| Const. | STRETCH | DIA(mil) [Size] | KNOT STRENGTH ABSOLUTE (lb) | KNOT STRENGTH INTRINSIC(psi) | % INCREASE INTRINSIC KNOT STRENGTH |
|---|---|---|---|---|---|
| 8 carrier 4 × 2 (13/15) | hot ( 8%) | 12.61 [2-0] | 4.73 | 37,800 | |
| core 2 × 2 (13/15) | wet (19%) | 11.62 | 4.56 | 43,000 | 13.5% |

-continued

| | | | | | |
|---|---|---|---|---|---|
| 16 carrier 2 × 2 (13/15) | hot ( 8%) | 15.56 [ 0 ] | 6.74 | 35,400 | |
| core 10 × 3 (13/15) | wet (15%) | 14.43 | 6.51 | 39,800 | 13.0% |

TABLE III
Black braided silk, stretched,
waxed, and Co$^{60}$ sterilized

| | | | | | |
|---|---|---|---|---|---|
| 8 carrier 4 × 2 (13/15) core 2 × 2 (13/15) | hot ( 8%) | 12.50 [2–0] | 4.47 | 36,400 | |
| 8 carrier 4 – 5 × 2 (13/15) & 4 – 3 × 3 (13/15); (no core) | wet (20%) | 12.44 | 4.93 | 40.500 | 11.0% |
| 8 carrier 2 × 2 (11/13) no core | hot ( 8%) | 7.45 [4–0] | 2.03 | 45,900 | |
| 8 carrier 2 × 2 (13/15) no core | wet (15%) | 7.25 | 2.20 | 52,600 | 14.7% |
| 16 carrier 4 × 2 (13/15) core 9 × 3 (20/22) | hot ( 8%) | 20.79 [ 2 ] | 10.27 | 30,200 | |
| 16 carrier 4 × 2 (13/15) core 12 × 3 (20/22) | wet (10%) | 20.00 | 11.42 | 36,300 | 20.0% |

TABLE II

| SIZE OF FINAL SUTURE | SPEED OF GODET ROLLS | | | | WATER TEMP. FOR PRESOAK & IMMERSION | DRYING GODET ROLL 18 TEMP. | PRESOAK TIME | WRAP ON DRYING GODET ROLL 18 |
|---|---|---|---|---|---|---|---|---|
| | 13,14 | 17 | 18 | 19,20 | | | | |
| 2–0 | 64.5 | 76.5 | 77.5 | 78.7 | room temp. | 250° F. | 24 hrs. | 9 |
| 4–0 | 67.6 | 75.2 | 77.4 | 79.0 | room temp. | 250° F. | 3–6 hrs. | 10 |
| 2 | 70.5 | 75.2 | 77.9 | 78.7 | room temp. | 250° F. | 3–6 hrs. | 10 |

This comparable final diameter for the hot-stretched and wet-stretched member of each pair was accomplished by employing for the wet-stretched member an experimental uncompacted braided silk suture having a larger initial diameter than the conventional uncompacted braided silk suture used for the hot-stretched member. As the wet-stretching caused a greater percentage stretch than did the hot-stretching, starting with an uncompacted suture of larger diameter for the wet-stretched member than for the hot-stretched member of each pair of sutures to be compared resulted in stretched sutures of comparable size, from both methods in each pair.

After stretching, all sutures were waxed and Co$_{60}$ sterilized as previously. The composition and strength data for these pairs of sutures are shown in Table III. Note that the composition of the wet-stretched size 2-0 suture is such that four carriers are 5 × 2 (13/15) and the other four are 3 × 3 (13/15). The wet-stretched sutures exhibited from 11 to 20% greater knot strength (psi) than the hot-stretched sutures of comparable diameters.

Table III presents comparative data for hot-stretched and wet-stretched sutures having comparable final diameters. By examination of the data in this table, one may clearly see the advantages which accrue from practice of the method of the present invention, notably the substantial increases in knot strength. Table III illustrates how it is possible to prepare according to the present invention a wet-stretched braided silk suture having a desired final diameter.

Although specific examples of the method and product of our invention have been disclosed above for illustrative purposes, it is not intended to limit the scope of my invention thereby. It is contemplated that any braided silk suture of whatever size or construction may be compacted by the method of the present invention to yield the product of the invention.

What is claimed is:

1. A process for compacting a braided silk suture which comprises: (1) presoaking an unstretched braided silk suture in a non-corrosive liquid for at least about one-half hour to wet the silk fibers; (2) stretching said presoaked suture, while the same is immersed in a non-corrosive liquid, until the suture is stretched from about 5 to about 35% of its original length; and (3) drying said stretched suture in a temperature range of from about 70° to about 300° F., while maintaining the same under tension.

2. A process for compacting a braided silk suture which comprises: (1) presoaking an unstretched braided silk suture in water for at least one-half hour; (2) stretching said presoaked suture, while the same is immersed in water, until the suture is stretched from about 5 to about 35% of its original length; and (3) drying said stretched suture in a temperature range of from 70° to about 300° F. while maintaining the same under at least sufficient tension to prevent any shrinkage taking place during the drying step.

3. A process for making a compacted braided silk suture which comprises: presoaking an unstretched braided silk suture in water for at least one-half hour; conducting said presoaked suture to a first pair of unheated, vertically aligned, fixedly-spaced Godet rolls rotating at the same peripheral speed; the lower of which rolls is at least partially immersed in water as it rotates; causing said suture to travel a multiplicity of times about said first pair of Godet rolls and finally under said lower roll; conducting said suture, while the same is immersed in water, to a second pair of rotating, vertically-aligned, fixedly-spaced Godet rolls, the lower of which rolls is unheated and is at least partially immersed in water as it rotates and is rotating at a greater peripheral speed than the rolls in said first pair of Godet rolls, and the upper of which second pair of rolls is heated and is rotating at no less than the sane peripheral speed as said lower roll of said second pair of rolls; causing said suture to travel a multiplicity of times about said lower roll of said second pair of rolls, whereby said suture is stretched while it is immersed in said water; conducting said suture to the upper heated Godet roll of said second pair of rolls; causing said suture to travel a multiplicity of times about said upper heated roll, whereby said suture is dried; conducting said suture to a third pair of unheated, fixedly-spaced Godet rolls rotating at the same peripheral speed, which peripheral speed is greater than the peripheral speed of said upper heated roll of said second pair of rolls and causing said suture to travel a multiplicity of times about said third pair of Godet rolls, thereby maintaining a tension on the suture while it is being dried; and conducting said suture to a wind-up spool.

* * * * *

UNITED STATES PATENT AND TRADEMARK OFFICE
CERTIFICATE OF CORRECTION

PATENT NO. : 4,014,973
DATED : March 29, 1977
INVENTOR(S) : Darrell A. Thompson

It is certified that error appears in the above-identified patent and that said Letters Patent are hereby corrected as shown below:

In Column 2, line 14, reads ... known strength... should read ... knot strength ...

In Column 3, line 26, reads ... compacted silk suture... should read ... compacted braided silk suture.

In Table III, Column 8, reads 40.500 should read -- 40,500 --.

In Claim 3, Column 8, line 65, reads ... no less than the sane... should read ...no less than the same ...

Signed and Sealed this

First Day of November 1977

[SEAL]

Attest:

RUTH C. MASON
*Attesting Officer*

LUTRELLE F. PARKER
*Acting Commissioner of Patents and Trademarks*